(12) United States Patent
Roberts (10) Patent No.: US 7,664,553 B2
(45) Date of Patent: Feb. 16, 2010

(54) SYSTEM AND METHOD FOR ENABLING COMMUNICATIONS WITH IMPLANTABLE MEDICAL DEVICES

(75) Inventor: Earle Roberts, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 601 days.

(21) Appl. No.: 11/116,108

(22) Filed: Apr. 27, 2005

(65) Prior Publication Data

US 2006/0247736 A1 Nov. 2, 2006

(51) Int. Cl.
*A61N 1/00* (2006.01)
(52) U.S. Cl. .......................... 607/60; 607/32
(58) Field of Classification Search ................ 607/32, 607/60; 128/903
See application file for complete search history.

(56) References Cited

U.S. PATENT DOCUMENTS

| | | | |
|---|---|---|---|
| 4,341,982 A | 7/1982 | Lahti et al. | |
| 4,404,972 A | 9/1983 | Gordon et al. | |
| 4,441,498 A | 4/1984 | Nordling | |
| 4,486,739 A * | 12/1984 | Franaszek et al. | 341/59 |
| 4,519,401 A | 5/1985 | Ko et al. | |
| 4,542,535 A | 9/1985 | Bates et al. | |
| 4,562,841 A | 1/1986 | Brockway et al. | |
| 4,944,299 A | 7/1990 | Silvian | |
| 5,113,869 A | 5/1992 | Nappholz et al. | |
| 5,171,977 A | 12/1992 | Morrison | |
| 5,300,093 A | 4/1994 | Koestner et al. | |
| 5,314,453 A | 5/1994 | Jeutter | |
| 5,342,408 A | 8/1994 | deCoriolis et al. | |
| 5,350,411 A | 9/1994 | Ryan et al. | |
| 5,486,200 A | 1/1996 | Lindemans | |
| 5,562,713 A | 10/1996 | Silvian | |
| 5,579,876 A | 12/1996 | Adrian et al. | |
| 5,683,432 A | 11/1997 | Goedeke et al. | |
| 5,694,952 A | 12/1997 | Lidman et al. | |

(Continued)

FOREIGN PATENT DOCUMENTS

WO WO-9500202 A1 1/1995

(Continued)

OTHER PUBLICATIONS

"International Search Report and Written Opinion for Application No. PCT/US2006/014957, Date mailed Sep. 29, 2006", 16 Pages.

(Continued)

*Primary Examiner*—George Manuel
*Assistant Examiner*—Christopher A Flory
(74) *Attorney, Agent, or Firm*—Schwegman, Lundberg & Woessner, P.A.

(57) ABSTRACT

A telemetry system is presented for enabling radio-frequency (RF) communications between an implantable medical device and an external device in a manner which reduces the power requirements of the implantable device by duty cycling its RF circuitry. A wakeup scheme for the implantable device is provided in which the external device transmits a data segment containing a repeating sequence of special wakeup characters and a device ID in order to establish a communications session with the implantable device. The wakeup scheme may be designed to operate using multiple communications channels.

10 Claims, 3 Drawing Sheets

U.S. PATENT DOCUMENTS

| | | | |
|---|---|---|---|
| 5,725,559 A | 3/1998 | Alt et al. | |
| 5,766,232 A | 6/1998 | Grevious et al. | |
| 5,807,397 A | 9/1998 | Barreras | |
| 5,843,139 A | 12/1998 | Goedeke et al. | |
| 5,861,019 A | 1/1999 | Sun et al. | |
| 5,881,101 A | 3/1999 | Furman et al. | |
| 6,009,350 A | 12/1999 | Renken | |
| 6,044,485 A | 3/2000 | Dent et al. | |
| 6,115,583 A | 9/2000 | Brummer et al. | |
| 6,115,636 A | 9/2000 | Ryan | |
| 6,167,310 A | 12/2000 | Grevious | |
| 6,169,925 B1 | 1/2001 | Villaseca et al. | |
| 6,240,317 B1 | 5/2001 | Villaseca et al. | |
| 6,263,246 B1 | 7/2001 | Goedeke et al. | |
| 6,336,903 B1 | 1/2002 | Bardy | |
| 6,385,318 B1 | 5/2002 | Oishi | |
| 6,388,628 B1 | 5/2002 | Dettloff et al. | |
| 6,416,471 B1 | 7/2002 | Kumar et al. | |
| 6,424,867 B1 | 7/2002 | Snell et al. | |
| 6,427,088 B1 | 7/2002 | Bowman, IV et al. | |
| 6,434,429 B1 | 8/2002 | Kraus et al. | |
| 6,443,891 B1 | 9/2002 | Grevious | |
| 6,456,256 B1 | 9/2002 | Amundson et al. | |
| 6,463,329 B1 | 10/2002 | Goedeke | |
| 6,470,215 B1 | 10/2002 | Kraus et al. | |
| 6,482,154 B1 | 11/2002 | Haubrich et al. | |
| 6,531,982 B1 | 3/2003 | White et al. | |
| 6,535,766 B1 | 3/2003 | Thompson et al. | |
| 6,564,104 B2 | 5/2003 | Nelson et al. | |
| 6,564,105 B2 | 5/2003 | Starkweather et al. | |
| 6,574,510 B2 | 6/2003 | Von Arx et al. | |
| 6,585,644 B2 | 7/2003 | Lebel et al. | |
| 6,600,952 B1 | 7/2003 | Snell et al. | |
| 6,602,191 B2 | 8/2003 | Quy | |
| 6,622,050 B2 | 9/2003 | Thompson | |
| 6,648,821 B2 * | 11/2003 | Lebel et al. | 600/300 |
| 6,659,948 B2 | 12/2003 | Lebel et al. | |
| 6,675,045 B2 | 1/2004 | Mass et al. | |
| 6,687,546 B2 | 2/2004 | Lebel et al. | |
| 6,763,269 B2 | 7/2004 | Cox | |
| 6,768,730 B1 | 7/2004 | Whitehill | |
| 6,801,807 B2 | 10/2004 | Abrahamson | |
| 6,868,288 B2 | 3/2005 | Thompson | |
| 6,970,735 B2 * | 11/2005 | Uber et al. | 600/431 |
| 6,985,773 B2 | 1/2006 | Von Arx et al. | |
| 6,993,393 B2 | 1/2006 | Von Arx et al. | |
| 7,013,178 B2 | 3/2006 | Reinke et al. | |
| 7,069,086 B2 | 6/2006 | Von Arx | |
| 7,110,823 B2 | 9/2006 | Whitehurst et al. | |
| 7,218,969 B2 * | 5/2007 | Vallapureddy et al. | 607/60 |
| 7,319,903 B2 * | 1/2008 | Bange et al. | 607/60 |
| 7,359,753 B2 | 4/2008 | Bange et al. | |
| 7,573,422 B2 * | 8/2009 | Harvey et al. | 342/357.06 |
| 2001/0047125 A1 | 11/2001 | Quy | |
| 2002/0019606 A1 | 2/2002 | Lebel et al. | |
| 2002/0046276 A1 * | 4/2002 | Coffey et al. | 709/224 |
| 2002/0049480 A1 | 4/2002 | Lebel et al. | |
| 2002/0065509 A1 | 5/2002 | Lebel et al. | |
| 2002/0065540 A1 | 5/2002 | Lebel et al. | |
| 2002/0109621 A1 | 8/2002 | Khair et al. | |
| 2002/0115912 A1 | 8/2002 | Muraki et al. | |
| 2002/0143372 A1 | 10/2002 | Snell et al. | |
| 2002/0147388 A1 | 10/2002 | Mass et al. | |
| 2003/0028902 A1 | 2/2003 | Cubley et al. | |
| 2003/0050535 A1 * | 3/2003 | Bowman | 600/300 |
| 2003/0083719 A1 | 5/2003 | Shankar et al. | |
| 2003/0114897 A1 | 6/2003 | Von Arx et al. | |
| 2003/0114898 A1 | 6/2003 | Von Arx et al. | |
| 2003/0146835 A1 | 8/2003 | Carter | |
| 2003/0149459 A1 | 8/2003 | Von Arx et al. | |
| 2004/0030260 A1 | 2/2004 | Von Arx | |
| 2004/0047434 A1 * | 3/2004 | Waltho | 375/308 |
| 2004/0260363 A1 | 12/2004 | Arx et al. | |
| 2005/0204134 A1 | 9/2005 | Von Arx et al. | |
| 2005/0222933 A1 * | 10/2005 | Wesby | 705/36 |
| 2005/0240245 A1 | 10/2005 | Bange et al. | |
| 2005/0283208 A1 | 12/2005 | Von Arx et al. | |
| 2005/0288738 A1 | 12/2005 | Bange et al. | |
| 2006/0025834 A1 | 2/2006 | Von Arx et al. | |
| 2006/0029100 A1 * | 2/2006 | Dove | 370/474 |
| 2006/0030901 A1 | 2/2006 | Quiles et al. | |
| 2006/0030902 A1 | 2/2006 | Quiles et al. | |
| 2006/0030903 A1 | 2/2006 | Seeberger et al. | |
| 2006/0030904 A1 * | 2/2006 | Quiles | 607/60 |
| 2006/0071756 A1 * | 4/2006 | Steeves | 340/10.1 |
| 2006/0116744 A1 | 6/2006 | Von Arx et al. | |
| 2006/0161223 A1 | 7/2006 | Vallapureddy et al. | |
| 2007/0100396 A1 * | 5/2007 | Freeberg | 607/60 |
| 2007/0185550 A1 * | 8/2007 | Vallapureddy et al. | 607/60 |
| 2008/0114412 A1 | 5/2008 | Bange et al. | |
| 2008/0215121 A1 | 9/2008 | Bange et al. | |

FOREIGN PATENT DOCUMENTS

| | | |
|---|---|---|
| WO | WO-03053515 A1 | 7/2003 |
| WO | WO-2005099816 A1 | 10/2005 |
| WO | WO-2005099817 A1 | 10/2005 |
| WO | WO 2006020546 A1 | 2/2006 |
| WO | WO-2006020549 A1 | 2/2006 |
| WO | WO-2006116004 A1 | 11/2006 |

OTHER PUBLICATIONS

Bange, Joseph E., et al., "Implantable Medical Device Telemetry With Adaptive Frequency Hopping" U.S. Appl. No. 11/456,937, filed Jul. 12, 2006, 35 pages.

Bange, Joseph E., et al., "Implantable Medical Device Telemetry With Periodic Frequency Hopping", U.S. Appl. No. 11/456,942, filed Jul. 12, 2006, 43 Pages.

Bange, Joseph E., et al., "System and Method for RF Wake-Up of Medical Device", U.S. Appl. No. 11/101,142, filed Apr. 7, 2005, 19 Pages.

Healy, S. J., et al., "System and Method for Providing Secure Exchange of Sensitive Information With an Implantable Medical Device", U.S. Appl. No. 10/801,150, filed Mar. 15, 2004, 30 pgs.

"European Application No. 06750873.9 Office Action mailed on May 7, 2009", 2.

* cited by examiner

SYSTEM AND METHOD FOR ENABLING COMMUNICATIONS WITH IMPLANTABLE MEDICAL DEVICES

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices (IMDs), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an IMD and an ED over a wireless medium. Such long-range RF telemetry allows the IMD to communicate with an ED, such as an external programmer or remote monitor, without the need for close proximity.

In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices.

It is also common in clinical settings for there to be multiple implantable and/or external devices present in an area so that communication over the wireless medium is possible between the multiple devices. Access to the medium among the multiple devices must be controlled in this situation in order for a communications session between any pair of devices to be established. It would also be desirable for there to be the possibility of multiple communications sessions between different devices occurring concurrently. Providing a means by which communications may be rapidly established with an IND in this environment within the constraints imposed by power conservation considerations, however, is problematic. Also, in either the home or the clinic, there are external sources of RF energy which may interfere with communication between the ED and IND, and this problem must also be dealt with.

SUMMARY

The present invention relates to a telemetry system for enabling radio-frequency (RF) communications between an implantable medical device and an external device in a multiple device environment in a manner which reduces the power requirements of the implantable devices. Each of the implantable devices is programmed to power up its transmitter and receiver for a specified time window at periodic intervals defined by the wakeup timer and wait for receipt of special wakeup characters transmitted by the external device. In order to wakeup and establish communications with only one selected implantable device among a plurality of such devices that are within range, an identification code unique to a particular implantable device is also transmitted by the external device. If the implantable device determines that its identification code has been transmitted, it then transmits an acknowledge signal and waits a specified period of time for a response from the external device. The external device and the implantable device then attempt to establish a communications session when a response to the acknowledge signal is received by the implantable device. Multiple communications channels separated in frequency may be used for narrow-band noise avoidance and to enable simultaneous communications sessions between devices. One or more of the multiple communications channels may be dedicated for use as control channels in transmitting the wakeup sequence and establishing a communications session.

DETAILED DESCRIPTION

Power consumption by an implantable device may be lessened by managing the duty cycle of the RF transmitting and receiving components. Long-range RF telemetry circuitry (i.e., the transmitter and receiver) typically requires power on the order of tens of milliwatts in order to operate. Implantable cardiac devices in use today, on the other hand, are usually designed to operate with average power in the microwatt range. This means that the RF telemetry circuitry must be duty cycled down in order to meet the power budget of such devices. The RF telemetry circuitry of an implantable device can either be powered up or down, referred to as awake and sleep states, respectively. Duty cycling of the implantable device's RF telemetry circuitry can be implemented by a wakeup timer which defines periodic wakeup intervals at which the implantable device powers up its RF circuitry and listens for a transmission from an external device for a specified period of time, referred to as a wakeup window. Upon acknowledging the transmission from the external device, a communications session can be established by a handshaking protocol, and data can then be transferred between the devices. In order to minimize power consumption, it is desirable for the RF circuitry of the implantable device to be powered up for as short a time as possible at each wakeup interval while still being able to reliably recognize session requests from the external device. If the implantable device recognizes a session request from the external device during its wakeup window, it remains awake long enough to establish a communications session with the external device; otherwise, the implantable device returns to a sleep state until the next wakeup interval occurs.

Described herein is a telemetry system for enabling radio-frequency (RF) communications between an implantable medical device and an external device in a multiple device environment in a manner which reduces the power requirements of the implantable device. In an exemplary system, the external device is programmed to transmit a data segment containing a repeating sequence of special wakeup characters in order to establish a communications session with the implantable device. The implantable device is programmed to power up its transmitter and receiver for a specified time window, referred to as a wakeup window, at periodic wakeup intervals defined by the wakeup timer and wait for receipt of one of the special wakeup characters transmitted by the external device. The implantable device maintains its transmitter and receiver in a powered-up state upon receipt of a special character and for as long as consecutive special wakeup characters continue to be received. In order to wakeup and establish communications with only one selected implantable device among a plurality of such devices that are within range, an identification code unique to a particular implantable device is also transmitted by the external device. In one embodiment, the identification code is included in the wakeup sequence so that a unique wakeup sequence is used to wakeup each implantable device. In another embodiment, the identification code is transmitted after one or more wakeup characters are transmitted. Once an implantable device is woken up by the wakeup characters, the device continues to receive data until it determines whether or not its identification code has been transmitted. If the implantable device determines that its identification code has been transmitted, it then transmits an acknowledge signal and waits a specified period of time for a response from the external device. When a response to the acknowledge signal is received by the implantable device, the external device and the implantable device are programmed to establish a communications session by a handshaking protocol. During a communications session, the RF transmitter and receiver of the implantable device may then either be maintained in the powered-up state for the duration of the communications session or powered down at prescribed intervals according to a defined protocol.

The controllers of the external and implantable devices may be programmed to operate their respective telemetry hardware in a manner which utilizes multiple communications channels. The multiple channels are defined with different carrier frequencies so that communications over one channel does not disturb communications over any of the other channels. By using multiple channels for data transfer, a plurality of communications sessions with different implantable devices may take place simultaneously. Also, most noise from external sources is of the narrow-band type, where the energy of the noise is confined to a particular frequency range. Examples of narrow-band noise sources include communications devices such as wireless telephones as well as many other kinds of electronic equipment which are commonly found in the home and in the clinic. When such narrow-band noise is in the same frequency range used for telemetry, it is said to be in-band and can interfere with communications between the devices. The use of multiple communications channels helps to alleviate this problem since, at any given time, only the channels at the same frequency as the in-band noise are interfered with. The devices may be programmed to test a channel for both noise and the presence of other traffic before using that channel for communications.

The wakeup scheme described above, however, requires the external device to use a channel for transmitting the wakeup sequence that is expected by the implantable device. A channel may therefore be dedicated to use for waking up and establishing communications with an implantable device, referred to as a wakeup channel or control channel, with the other channels used for data communications referred to as data channels. Once a communications session is established, the external device finds an available and non-noisy data channel and transmits the information to the implantable device so that both devices can switch to that channel for data transfer. The control channel is then freed up for use by other devices in establishing communications sessions. In another embodiment, multiple control channels are employed in order to allow for the possibility that narrow-band noise could render a single control channel unusable. The implantable device in that case may be programmed to power up its receiver and listen for wakeup characters on the different control channels. The wakeup intervals for the different control channels could be the same or different.

1. Exemplary Hardware Components

Figure 1:
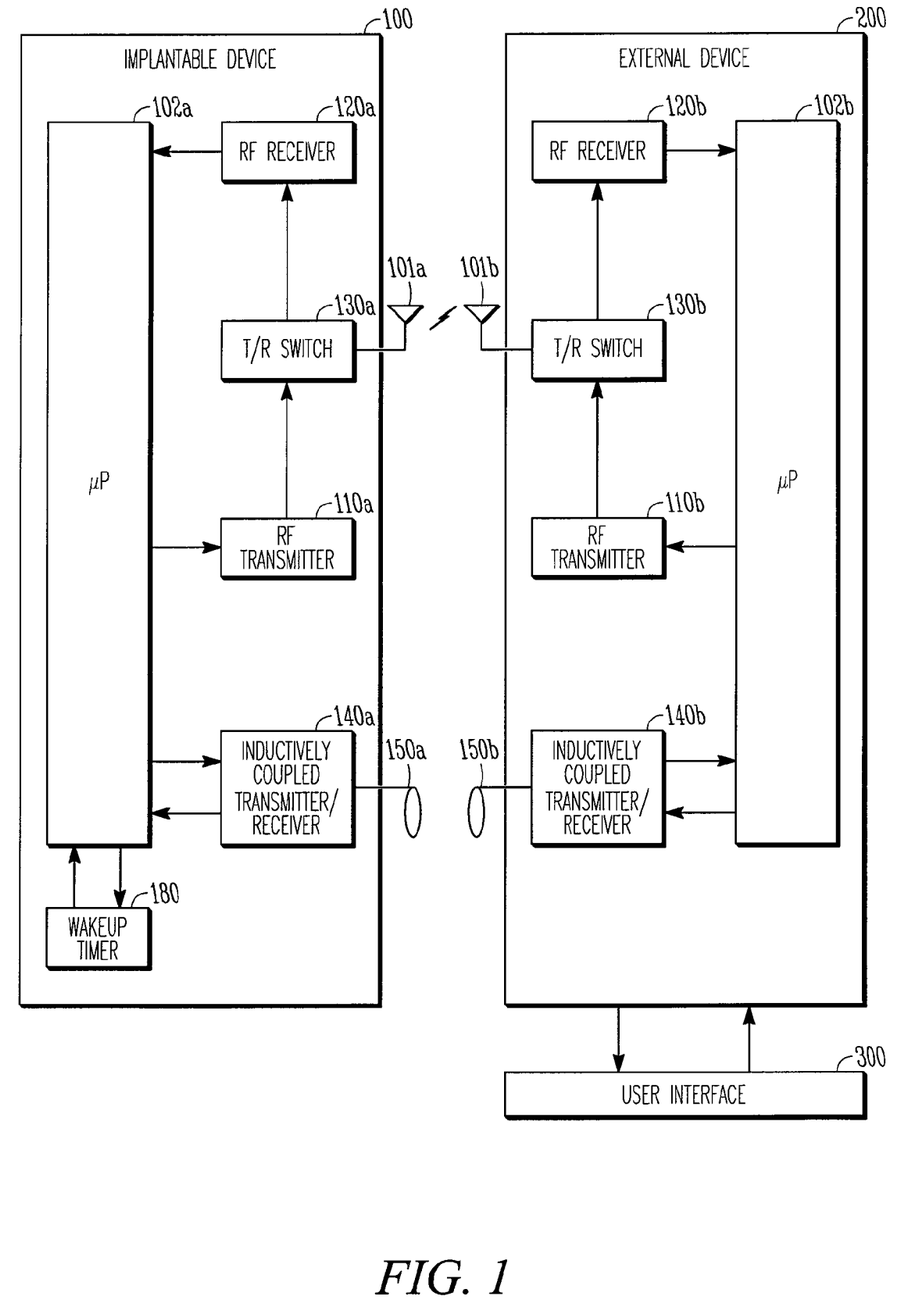
FIG. 1 is a block diagram of a telemetry system for an implantable device and an external device.

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the duty cycle management schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles in the manner described below. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place without concern for power consumption when the two devices are in close physical proximity to one another.

2. Description of Communications Enablement Scheme

Figure 2:
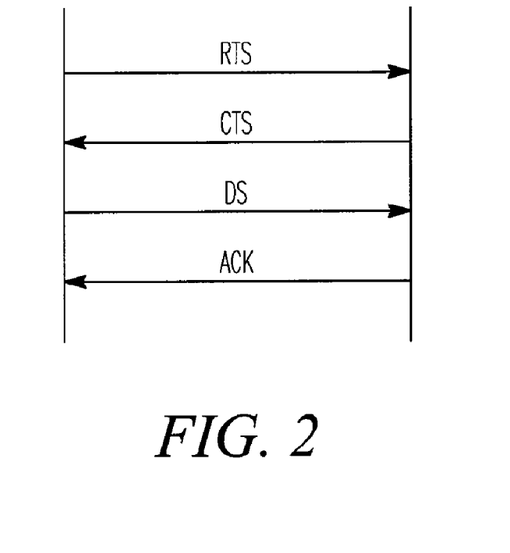
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) frame and waits a defined period of time for a clear-to-send (CTS) frame from the intended recipient. All other network participants who hear either of the RTS or CTS frames defer their transmissions. Upon receiving the CTS response, the sender can assume that the medium has been exclusively acquired and can then begin transmission of a data segment (DS) to the recipient. If the data is received without errors, the recipient responds with an acknowledge (ACK) frame which frees the medium for access by another participant. The present invention, in various embodiments, may work in the context of any of the medium access control protocols discussed above.

Figure 3:
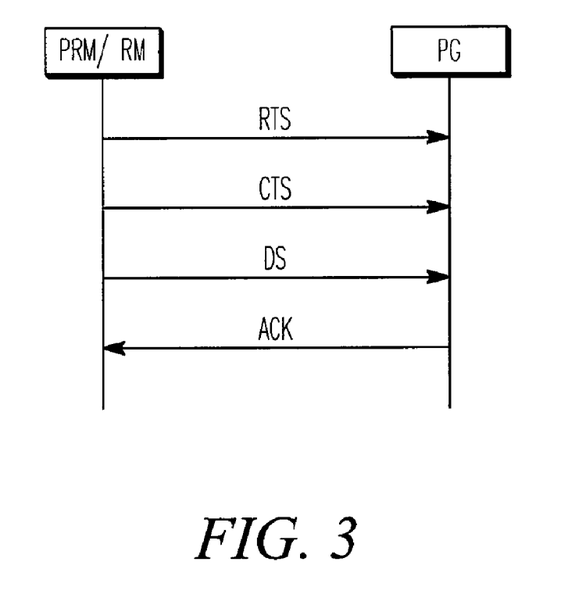
FIG. 3 illustrates a wakeup scheme in accordance with the invention.

A particular communications enablement scheme will now be described with reference to an external programmer or remote monitor (PRM/RM) and an implantable device (referred to as a pulse generator or PG). In this embodiment, the wakeup process works within the framework of a handshaking collision avoidance protocol as described above. In such a protocol, the PRM/RM transmits the RTS and CTS frames to cause other participants to defer their transmissions. It then transmits a data segment DS containing wakeup characters and a device ID to the particular PG it wants to communicate with. The awakened PG then transmits an ACK frame to release the medium. The wakeup process is illustrated by FIG. 3. The length of the DS message is set to a large number (e.g., 256 bytes), and contains a repeating sequence of a special n-bit (e.g., 10-bit) character reserved solely for use as a wakeup indicator. In one embodiment, the implantable device and the external device communicate by a transmission code which provides a DC balanced data stream such as 8b/10b. Such bit balanced data streams are advantageous in RF communications. In order for the special wakeup character to be invariant, the special wakeup character may be selected as a bit balanced sequence which is not changed by the transmission code.

The data segment also contains a device ID which may be either incorporated into the wakeup indicator itself by employing unique wakeup characters for each PG or may be a separate sub-segment transmitted after the wakeup characters. The PG wakes up periodically (e.g., every 20-30 seconds) and listens for a very short interval to receive a wakeup special character. If one wakeup special character is received, then the PG will stay awake long enough to receive several more wakeup special characters. In one embodiment, the wakeup characters are unique to the PG, and the awakened PG knows that the PRM/RM wants to establish a communications session with it. The PG then remains awake after the data segment is finished and transmits an ACK frame to the PRM/RM. In another embodiment, the awakened PG waits for a device ID which occurs later in the data segment, and it goes back to a sleep state if the device ID does not match its own. Otherwise, the PG remains awake after the data segment and responds with an ACK frame. After transmitting the ACK frame, the PG then stays awake for an extended period of time in order to receive a response from the PRM/RM. The PRM having successfully received this ACK message proceeds to perform a connection process which will contend for message traffic within the protocol framework in order to establish a communications session with the PG.

Figure 4:
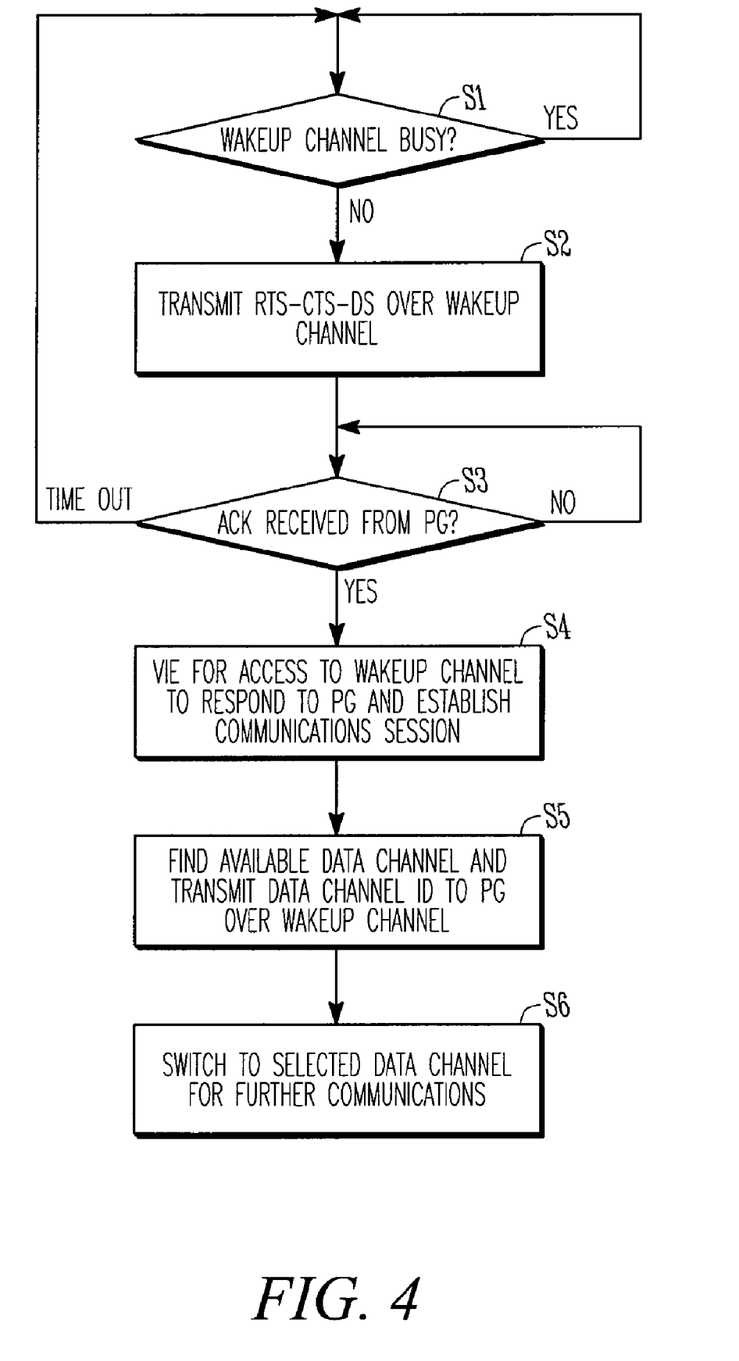
FIG. 4 illustrates the steps performed by the PRM/RM in establishing a communications session in the multiple channel environment.

The communications scheme just described enables a PRM/RM to establish a communications session with a selected one among a plurality of PG's using a single communications channel which is shared among the PG's. In further modification, the communications system utilizes multiple communications channels separated in frequency. One of the channels is dedicated for use as a control or wakeup channel with the other channels used as data channels for continuing communications sessions established over the wakeup channel. FIG. 4 illustrates the steps performed by the PRM/RM in establishing a communications session in the multiple channel environment. The PG's are configured to periodically wake up and listen for wakeup characters on the wakeup channel in the manner described above. At step S1, the PRM/RM waits until it determines that the wakeup channel is available (e.g., by receiving an ACK frame from some other device on the channel or by determining that there is no traffic on the channel). At step S2, it transmits the RTS-CTS-DS sequence over the wakeup channel, where the DS frame includes the device ID of the PG it wants to communicate with as described above. At step S3, the PRM/RM waits for an ACK from the PG. If no ACK is received after a specified period of time, a time out is declared and the device returns to step S1 to transmit another wakeup sequence. Otherwise, after receiving the ACK frame, the PRM/RM at step S4 vies for access to the wakeup channel in order to respond to the PG and establish a communications session. At step S5, the PRM/RM then finds an available data channel and transmits the data channel ID to the PG over wakeup channel. At step S6, the PRM/RM and PG both switch to the selected data channel for further communications.

By having multiple data channels, the system allows data communications to take place in the event narrow-band noise renders one of the channels unusable. It may also be desirable to use multiple wakeup channels so that communications sessions can be initiated with a PG in the event that narrow-band noise corrupts one of the wakeup channels. In this embodiment, the PG may be programmed to wake up and listen for wakeup characters on each of the wakeup channels. The wakeup intervals at which the PG wakes up and listens on each of the wakeup channels may be the same or different. For example, the PG may wakeup every minute to listen for wakeup characters on a primary wakeup channel and wakeup every three minutes to listen on a secondary wakeup channel. The PRM/RM would then be programmed to transmit the wakeup sequence on the primary and secondary wakeup channels either alternately or simultaneously.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A telemetry system for enabling radio-frequency (RF) communications between an implantable medical device and an external device, comprising:

an antenna, an RF transmitter, an RE receiver, and a controller incorporated into each of the implantable and external devices;

a wakeup timer incorporated into the implantable device;

wherein the RF transmitter and receiver of the implantable device are interfaced to the controller in the implantable device to enable the RF transmitter and receiver of the implantable device to be powered up or down;

wherein the external device is programmed to transmit a data segment containing a repeating sequence of special wakeup characters and a device ID in order to establish a communications session with the implantable device;

wherein the implantable device is programmed to operate its transmitter and receiver according to a timed duty cycle by being programmed to power up its transmitter and receiver for a specified time window at periodic intervals defined by the wakeup timer and wait for receipt of one of the special wakeup characters transmitted by the external device;

wherein the implantable device is programmed to suspend operation of the timed duty cycle and wakeup timer, maintain its transmitter and receiver in a powered-up state upon receipt of a special character prior to receipt of the device ID and prior to establishment of a communications session and for as long as consecutive special wakeup characters continue to be received, transmit an acknowledge signal to the external device if the device ID matches its own ID, and wait a specified period of time for a response from the external device; and, wherein the external device and the implantable device are programmed to establish a communications session when a response to the acknowledge signal is received by the implantable device.

2. The system of claim 1 wherein the device ID is incorporated into the wakeup characters by using unique wakeup characters for a particular implantable device.

3. The system of claim 1 wherein the device ID is included in the data segment after the wakeup characters.

4. The system of claim 1 wherein the RF transmitter and receiver of the external and implantable devices may be switched among multiple communications channels separated in frequency.

5. The system of claim 4 wherein one of the multiple channels is dedicated for use as a wakeup channel for establishing a communications session and the remaining channels are data channels for continuing established communications sessions.

6. The system of claim 5 wherein the external device is programmed to transmit an RTS frame, a CTS frame, and the data segment over the wakeup channel, the implantable device is programmed to respond by transmitting an ACK frame over the wakeup channel.

7. The system of claim 6 wherein the external device is programmed, after receiving the ACK frame from the external device over the wakeup channel, to vie for access to the wakeup channel in order to respond to the implantable device and establish a communications session.

8. The system of claim 7 wherein the external device is programmed, after establishing a communications session with the implantable device, to find an available data channel, transmit a data channel ID to the implantable device over wakeup channel, and switch to the selected data channel for further communications.

9. The system of claim 1 wherein the implantable device and the external device communicate by a transmission code which provides a DC balanced data stream.

10. The system of claim 9 where the transmission code is 8b/10b.

* * * * *

UNITED STATES PATENT AND TRADEMARK OFFICE
CERTIFICATE OF CORRECTION

PATENT NO. : 7,664,553 B2 Page 1 of 1
APPLICATION NO. : 11/116108
DATED : February 16, 2010
INVENTOR(S) : Earle Roberts It is certified that error appears in the above-identified patent and that said Letters Patent is hereby corrected as shown below:

In column 7, line 22, in Claim 1, delete "RE" and insert -- RF --, therefor.

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,664,553 B2
APPLICATION NO. : 11/116108
DATED : February 16, 2010
INVENTOR(S) : Earle Roberts It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this

Twenty-eighth Day of December, 2010

David J. Kappos
*Director of the United States Patent and Trademark Office*